United States Patent [19]

Petersen

[11] Patent Number: 5,342,368
[45] Date of Patent: Aug. 30, 1994

[54] INTRAMEDULLARY UNIVERSAL PROXIMAL TIBIAL RESECTOR GUIDE

[76] Inventor: Thomas D. Petersen, 9680 Alto Dr., La Mesa, Calif. 92041

[21] Appl. No.: 910,568

[22] Filed: Jul. 8, 1992

[51] Int. Cl.⁵ ............................................... A61F 5/04
[52] U.S. Cl. .......................................... 606/88; 606/87
[58] Field of Search ..................................... 606/86–89, 606/79, 80, 81, 82, 83, 96, 97, 98, 62, 102

[56] References Cited

U.S. PATENT DOCUMENTS

| 4,567,886 | 2/1986 | Petersen | 606/88 |
| 4,759,350 | 7/1988 | Dunn | 606/82 |
| 4,945,904 | 8/1990 | Bolton | 606/96 |
| 4,952,213 | 8/1990 | Bowman | 606/88 |
| 5,049,149 | 9/1991 | Schmidt | 606/87 |
| 5,053,039 | 10/1991 | Hofmann | 606/87 |
| 5,211,645 | 5/1993 | Baumgart | 606/96 |
| 5,228,459 | 7/1993 | Caspari | 606/87 |

FOREIGN PATENT DOCUMENTS

415837  3/1991  European Pat. Off. .............. 606/87

Primary Examiner—Robert A. Hafer
Assistant Examiner—David Kenealy
Attorney, Agent, or Firm—H. Jay Spiegel

[57] ABSTRACT

An intramedullary universal proximal tibial resector guide is disclosed which combines several unique features together to provide an extremely versatile instrument. The inventive guide includes structure allowing anterior-posterior adjustment, medial-lateral adjustment, posterior slope adjustment and vertical adjustment. The design of the precision slot of the present invention best facilitates resection of the proximal tibia beneath the patellar fat pad. The vertical adjustment utilizes a micrometer-type actuator to allow precise adjustment of the appropriate cutting depth. Deep grooves on the intramedullary rod facilitate decompression of the intramedullary fat. The resector cutting head may be removed from the rest of the instrument in an easy one-step procedure leaving the resector cutting head in place ready to receive a surgical resection cutting blade.

13 Claims, 6 Drawing Sheets

INTRAMEDULLARY UNIVERSAL PROXIMAL TIBIAL RESECTOR GUIDE

BACKGROUND OF THE INVENTION

The present invention relates to an intramedullary universal proximal tibial resector guide. Resector guide devices are known in the prior art. However, Applicant is unaware of any such device including all of the features and aspects of the present invention.

The following prior art is known to Applicant:

U.S. Pat. No. 4,457,307 to Stillwell discloses a bone cutting device for total knee replacement, including an adjustable carriage for a bone cutting saw designed to be used to make the various cuts on the distal femur and the proximal tibia for the purpose of installing a total knee prosthesis. The Stillwell device is designed to be attached to the distal femur and is adjustable in various directions and orientations to perform all of the necessary cuts. The present invention differs from the teachings of Stillwell as attaching in an intramedullary manner to the proximal tibia, as providing a guide for a separate saw rather than a carriage carrying a saw and as providing stepped adjustment of the posterior slope of the saw guide.

U.S. Pat. No. 4,474,177 to Whiteside discloses a method and apparatus for shaping a distal femoral surface. Since the present invention is directed to the proximal tibia, the Whiteside patent is believed to be of only general interest.

Applicant's U.S. Pat. No. 4,524,766 discloses a surgical knee alignment method and system for making the various cuts necessary in knee replacement surgery including cuts of the proximal tibia through the use of a tibial resection guide head. The present invention differs from the teachings of this patent as utilizing intramedullary fixation, as providing simple one-step disengagement of the cutting guide head from the rest of the instrument and as being limited to cuts of the proximal tibia.

U.S. Pat. No. 4,567,885 to Androphy discloses a triplanar knee resection system designed for use in resecting the distal femur as well as the proximal tibia. Androphy does not contemplate any adjustment of the posterior slope of the proximal tibial cut. Furthermore, Androphy fails to contemplate the structure of the various other adjustments incorporated into the present invention including anterior-posterior, medial-lateral, vertical (depth of cut). As such, the Androphy patent is believed to be of only general interest concerning the teachings of the present invention.

U.S. Pat. No. 4,574,794 to Cooke et al. discloses an orthopaedic bone cutting jig and alignment device which is attached to the leg of the patient through the use of a multiplicity of pins. The Cooke et al. device is shown as being supported on a horizontal base plate 1. The present invention differs from the teachings of Cooke et al. as contemplating support of the device using an intramedullary rod inserted into the tibia from the proximal end thereof. The present invention is also structurally distinct from the teachings of Cooke et al. as will be described in greater detail hereinafter.

U.S. Pat. No. 4,703,751 to Pohl discloses a method and apparatus for resecting a distal femoral surface. The present invention differs from the teachings of Pohl as being directed to the proximal tibia, as including adjustments in all degrees of freedom along with alignment with a mechanical axis of the leg.

U.S. Pat. No. 4,722,330 to Russell et al. discloses a femoral surface shaping guide for knee implants. Since the present invention is specifically intended to be used in guiding cuts of the proximal tibia, it is believed that the Russell et al. teachings are of only general background interest.

U.S. Pat. No. 4,750,481 to Reese discloses osteotomy appliances and method for correcting bone deformities. This reference is believed to be of only general interest.

U.S. Pat. No. 4,787,383 to Kenna discloses prosthetic knee implantation including means for resection of the distal femur as well as the proximal tibia. The present invention differs from the teachings of Kenna as providing a proximal tibial resector guide attachable to the tibia through the use of an intramedullary rod, alignable with a mechanical axis of the leg via a telescoping rod and including specific structure of stepped adjustment of the posterior slope of the proximal tibial cut.

U.S. Pat. No. 4,938,762 to Wehrli discloses a reference system for implantation of condylar total knee prostheses. The present invention differs from the teachings of Wehrli as contemplating a proximal tibial resector guide which is attached through insertion of an intramedullary rod in through an opening formed in the proximal tibia, with the present invention including a saw guide which may be easily removed from the rest of the resector guide structure, and as contemplating specific structure for adjustments in all degrees of freedom.

U.S. Pat. No. 4,952,213 to Bowman et al. discloses a tibial cutting guide including the provision of an intramedullary rod with vertical adjustment of the cutting guide acting upon the intramedullary rod and with other adjustments being provided. The present invention differs from the teachings of Bowman et al. as contemplating a proximal tibial resector guide which, while having an intramedullary rod, contemplates vertical adjustments being undertaken through structure separate and apart from the intramedullary rod. Other structural distinctions also exist.

Applicant herein is co-applicant along with Todd Johnson, Richard Lane, Chuck Nichols and John Howard in U.S. patent application Ser. No. 07/805,696 filed Dec. 10, 1991 for an extramedullary TIBIAL RESECTOR GUIDE. The present invention differs from the teachings of this application as requiring intramedullary fixation and due to its unique structure for adjustment of a saw guide in the vertical, anterior-posterior and medial-lateral directions.

SUMMARY OF THE INVENTION

The present invention relates to an intramedullary universal proximal tibial resector guide. The present invention includes the following interrelated objects, aspects and features:

(A) In a first aspect, the present invention is fixated to the proximal tibia through the use of an intramedullary rod. The rod incorporates deep grooves which extend longitudinally thereof and are specifically designed and provided to facilitate decompression of the intramedullary fat.

(B) A bar is rigidly fixed to the proximal end of the intramedullary rod and extends away from the intramedullary rod at a right angle thereto. The bar has a thin rectangular cross-section and is provided to carry the saw guide and all of the structures provided for making the various positional adjustments thereto.

(C) A hollow sleeve is provided with a longitudinal opening sized to frictionally receive the outer periphery of the perpendicular bar so that the sleeve may slide back and forth on the bar to provide anterior posterior adjustment for the instrument. The sleeve may be slid along the bar to any desired location and when let go is frictionally retained in position. Contained within the hollow sleeve is an elongated rod which is externally threaded at its proximal end, which end is threadably received within the interiorly threaded passageway in an adjustment knob which sits on top of the hollow sleeve. Thus, rotations of the adjustment knob result in reciprocations of the threaded rod to thereby provide vertical adjustment to the inventive saw guide and thereby adjustment of the depth of cut.

(D) The distal end of the threaded rod includes an enlargement comprising a flat plate having an opening therethrough allowing mounting thereto of the forked proximal end of structure permitting medial-lateral adjustment of the saw guide. The forked proximal end of the above-described structure is pivotably mounted to the flat plate of the distal end of the threaded rod by virtue of a mounting pin. A tightening knob is provided which may frictionally engage one of the forks of the proximal end of the above-described structure to retain the saw guide in a particular orientation of medial-lateral adjustment. In addition, a telescoping rod is removably attachable to the structure for providing medial-lateral adjustment so that medial-lateral adjustment may be carried out taking into account the location of the ankle of the patient and, thereby, the mechanical axis of the patient's tibia. After the medial-lateral adjustment has been made with the telescoping rod attached, and the tightening knob has been tightened to maintain the medial-lateral position of the guide, the telescoping rod may easily be removed.

(E) The above-described structure for medial-lateral adjustment also carries a device allowing stepped adjustment of the posterior slope angle of the saw guide. The stepped adjustment allows the user to adjust the angle of posterior slope to any one of 0°, 3°, 5°, 7° or 10°. The operation of the posterior slope adjustment includes a slide received within a dovetail groove which causes pivoting of an L-shaped support for the saw guide.

(F) The longer leg of the L-shaped support carries the saw guide and includes a coupling mechanism allowing one-step removal of the saw guide from the rest of the structure of the inventive intramedullary universal proximal tibial resector guide. The actual saw guide is coupled to the L-shaped structure by virtue of a pin received within a hole and an elongated threaded shaft having a knob allowing the shaft to be inserted to couple the saw guide to the L-shaped structure and to be reciprocated to remove the threaded shaft to allow easy detachment of the saw guide. In this way, all of the various adjustments discussed above may be carried out to precisely locate the saw guide in its desired location whereupon the saw guide may be pinned in place through the use of a plurality of openings formed therethrough, whereupon the saw guide may be detached from the rest of the structure of the intramedullary universal proximal tibial resector guide to permit the surgeon an unrestricted view of the surgical site.

As such, it is a first object of the present invention to provide an intramedullary universal proximal tibial resector guide.

It is a further object of the present invention to provide such a device allowing variable posterior slope resection within the range of 0° to 10°.

It is a still further object of the present invention to provide such a device which includes intramedullary fixation.

It is a still further object of the present invention to provide such a device including anterior-posterior adjustment as well as medial-lateral adjustment.

It is a yet further object of the present invention to provide such a device having a micrometer adjustment of the vertical cutting height.

It is a yet further object of the present invention to provide such a device including easy one-step removal of the saw guide from the rest of the instrument.

These and other objects, aspects and features of the present invention will be better understood from the following detailed description of the preferred embodiment when read in conjunction with the appended drawing figures.

SPECIFIC DESCRIPTION OF THE PREFERRED EMBODIMENT

Figure 1:
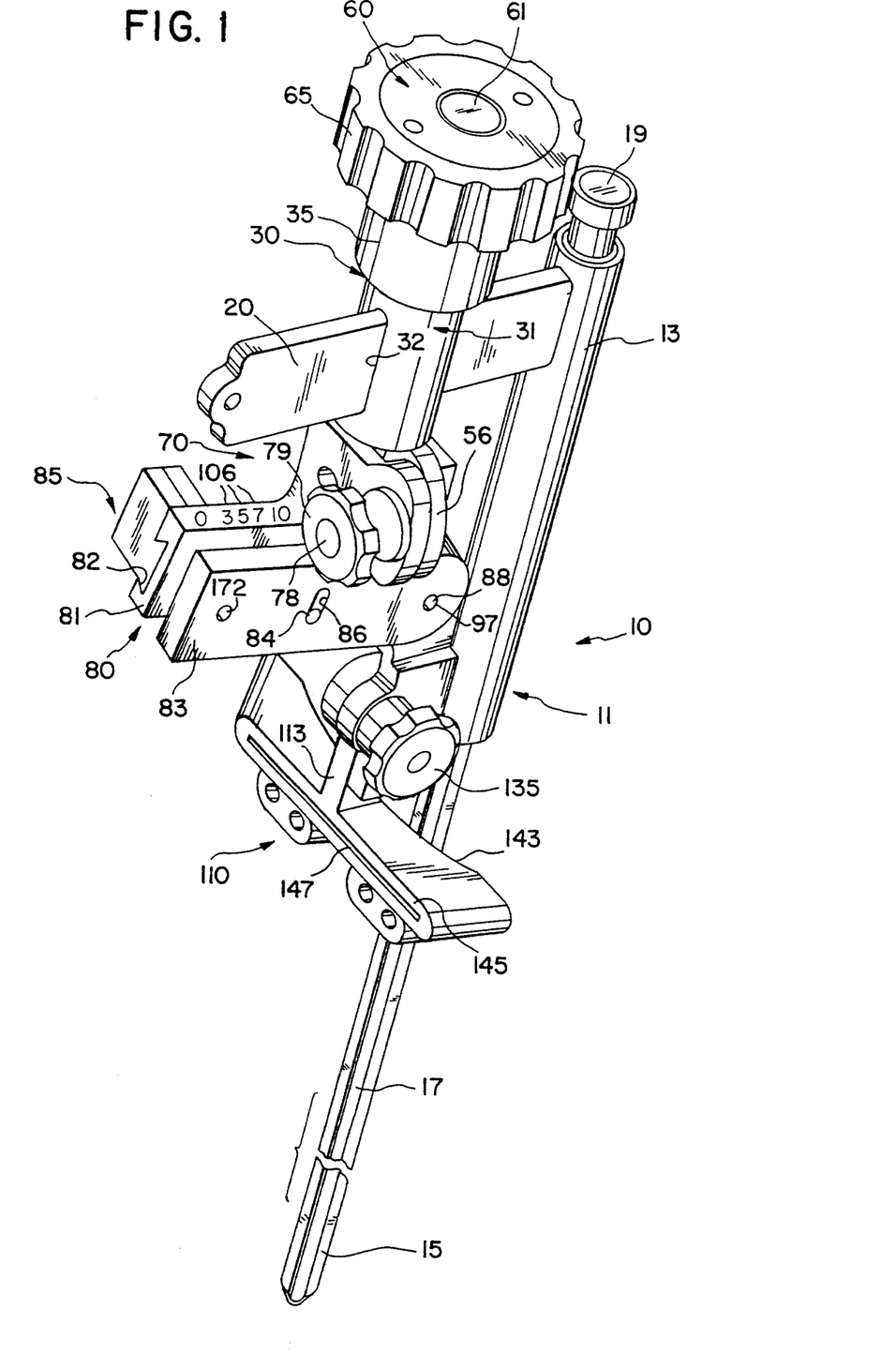
FIG. 1 shows a perspective view of the present invention.
Figure 2:
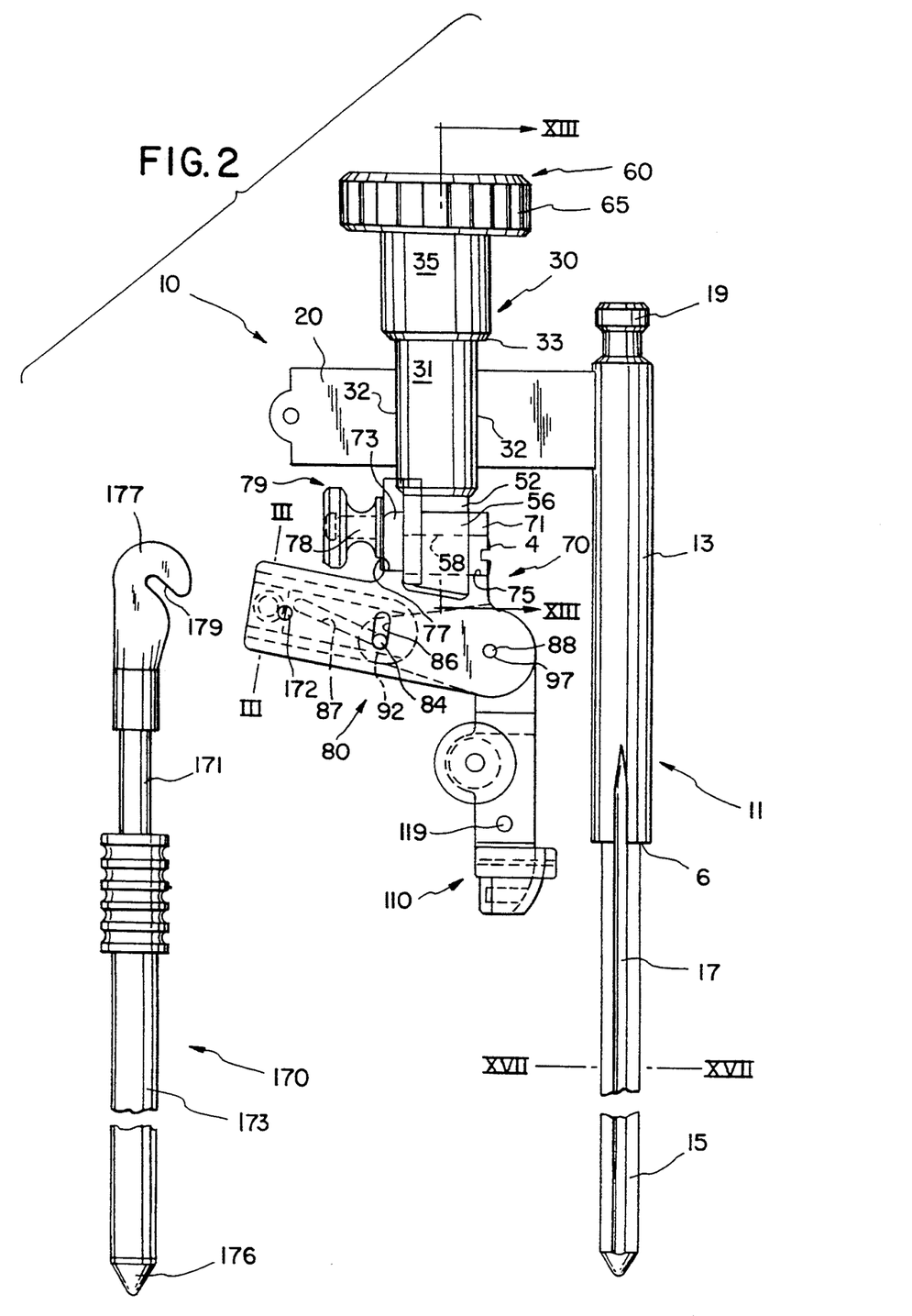
FIG. 2 shows a side view of the present invention including the telescoping rod.

With reference, first, to FIGS. 1 and 2, the present invention is generally designated by the reference numeral 10 and is seen to include an elongated intramedullary rod 11 having a proximal end 13 and a distal end 15. As seen in the figures, the distal end 15 of the intramedullary rod 11 has two opposed longitudinal grooves 17 of which one is seen in FIGS. 1 and 2.

Figure 17:
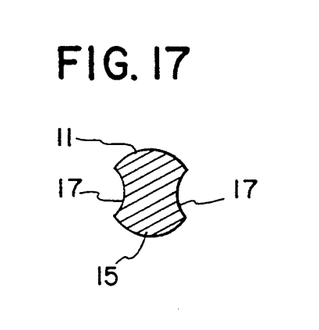
FIG. 17 shows a cross-sectional view along with line XVII—XVII of FIG. 2.

With reference to FIG. 17, it is seen that the grooves 17 are arcuate in cross-section and are specifically provided so that when the intramedullary rod is inserted within the tibia from the proximal end thereof, decompression of intramedullary fat occurs to make the insertion of the intramedullary rod 11 less intrusive. The proximal end 13 of the intramedullary rod 11 also includes a knob-like protrusion 19 which is designed for easy impact insertion and may be gripped by a suitable extraction device for extraction.

With further reference to FIGS. 1 and 2, it is seen that an elongated bar 20 is rigidly affixed to the proximal end 13 of the intramedullary rod 11 and extends away therefrom in a perpendicular direction.

Figure 13:
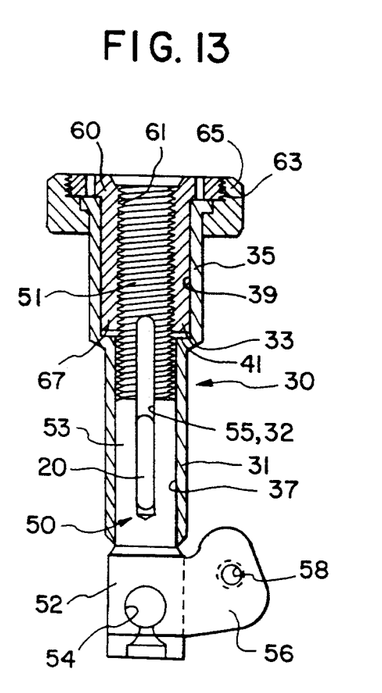
FIG. 13 shows a cross-sectional view along the line XIII—XIII of FIG. 2.

As best seen with reference to FIGS. 1 and 13, the elongated bar 20 has a thin generally rectangular cross-section.

With reference, now, to FIGS. 1, 2 and 13, it is seen that an elongated sleeve 30 is slidably mounted on the elongated bar 20 with the longitudinal axis of the sleeve 30 being perpendicular to the direction of extension of the bar 20 and being parallel to the longitudinal extent of the intramedullary rod 11. The sleeve 30 includes a smaller diameter portion 31 which is connected to a larger diameter portion 35 at a shoulder 33. The smaller diameter portion 31 has a longitudinal bore 37 while the larger diameter portion 35 has a longitudinal larger bore 39 which terminates at a shoulder 41. The smaller diameter portion 31 of the elongated sleeve 30 has two elongated slots 32 which are specifically sized to frictionally engage the outer walls of the elongated bar 20 so that the elongated sleeve 30 may be slid over the elongated bar 20 but will be frictionally retained in any desired position.

With reference back to FIG. 13, it is seen that an elongated rod 50 has a proximal threaded portion 51 and a distal portion 53 having a smooth periphery. The distal portion 53 smooth outer periphery is sized to be slidably received within the bore 37 of the portion 31 of the sleeve 30. The proximal threaded end 51 of the rod 50 is threadably received within a threaded bore 61 of an actuator sleeve 60 rotatably received within the enlarged bore 39 of the elongated sleeve 30. The sleeve 60 includes a threaded periphery 63 threadably receiving gripping knob 65. The threaded bore 61 extends throughout the longitudinal extent of the sleeve 60 with the sleeve 60 having a lower terminus 67 which sits on the shoulder 41 defining the end of the bore 39. Thus, rotative movements of the knob 65 and sleeve 60 result in corresponding reciprocations of the rod 50 in directions dependent upon the direction of rotation of the knob 65. In addition, the rod 50 includes an elongated slot 55 through which the bar 20 extends so as to allow the sleeve 30 to reciprocate on the bar 20 and also to constrain movements of the rod 50 so that the rod 50 may only reciprocate and may not rotate.

As seen in FIG. 13, the rod 50 includes a distal end 52 having an opening 54 therethrough as well as a laterally directed arcuately shaped plate 56 having an opening 58 therethrough for a purpose to be described in greater detail hereinafter.

Figure 14:
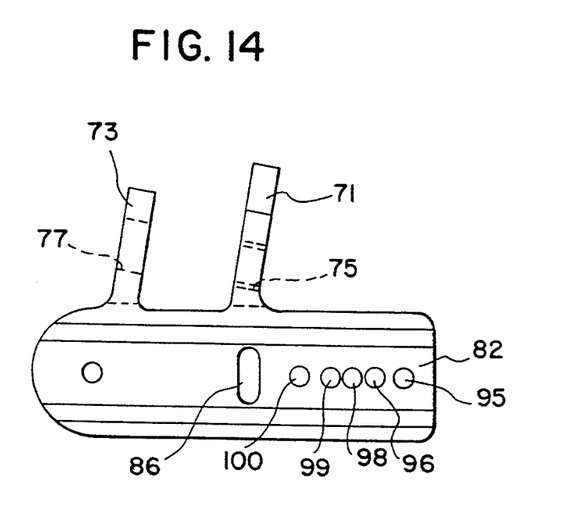
FIG. 14 shows a side view of a portion of the structure permitting posterior slope adjustment.

With reference, now, in particular, to FIGS. 1, 2 and 14, a medial-lateral adjustment structure is generally designated by the reference numeral 70 and is seen to include a forked proximal end having upwardly extending legs 71 and 73 which are mounted in surrounding relation to the plate 56 attached to the elongated rod 50 and are rotatably mounted thereto through the use of an elongated fastener 4 extending through aligned openings 75 and 77 as well as the opening 58 in the plate 56 as seen in FIG. 13. As should be understood, the bore 77 is threaded and complementary threads on the end of the fastener 4 permit attachment in the manner particularly shown in FIG. 2 while allowing pivoting of the structure 70 with respect to the rod 50 in the medial-lateral direction.

A knob 79 includes a threaded shaft 78 which extends between the leg 73 and the plate 56 to allow the knob 79 to be tightened to hold the structure 70 in any position in the medial-lateral direction.

Figures 3, 4, 5, 6, 7, 8:
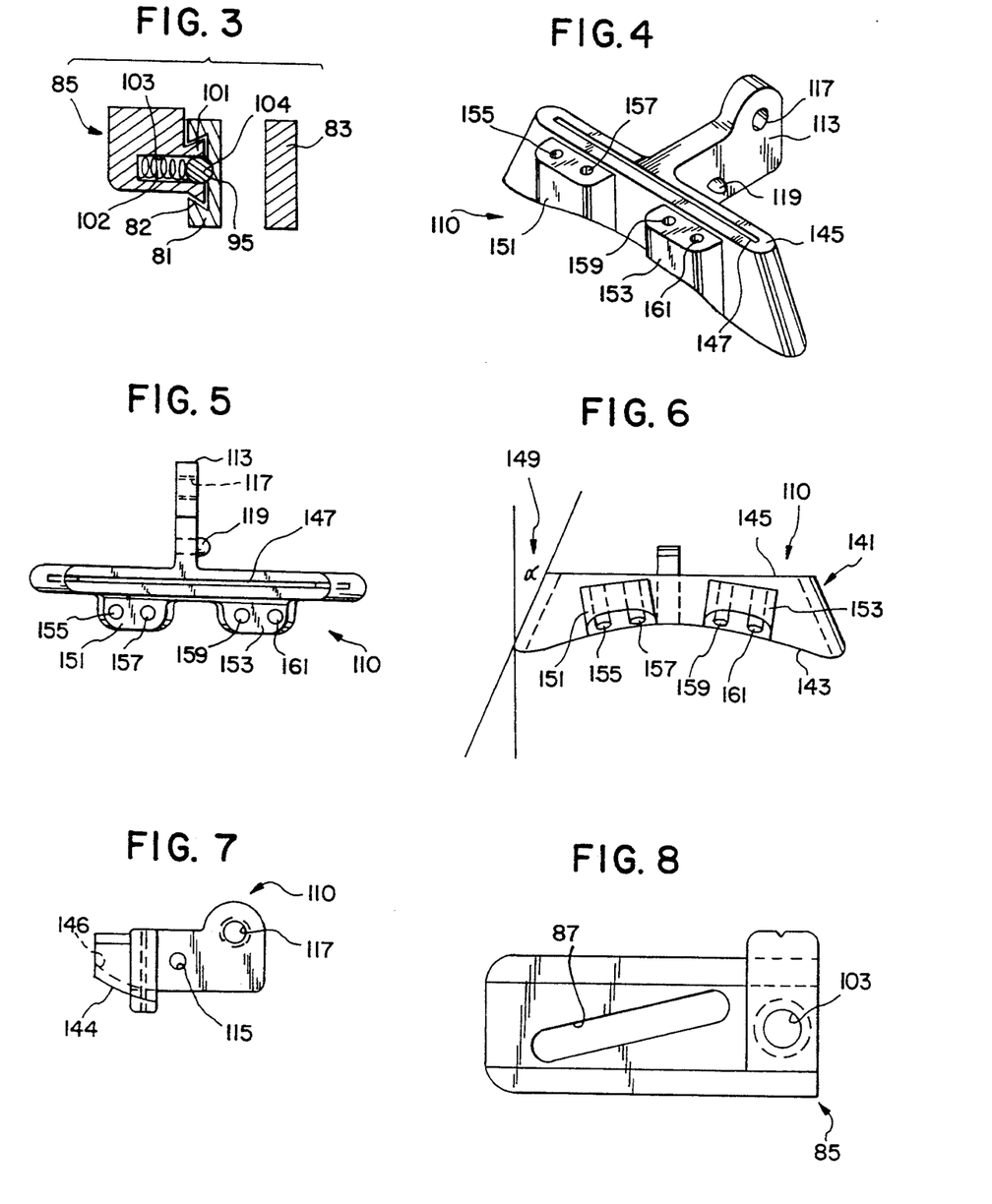
FIG. 3 shows a cross-sectional view along the line III—III of FIG. 2.
FIG. 4 shows a perspective view of the saw guide.
FIG. 5 shows a front view of the saw guide.
FIG. 6 shows a bottom view of the saw guide.
FIG. 7 shows a side view of the saw guide.
FIG. 8 shows a side view of a slide mechanism utilized in adjusting the posterior slope of the saw guide.
Figure 9:
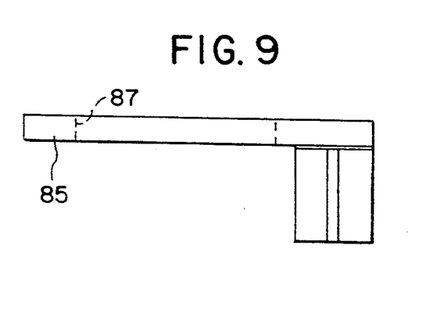
FIG. 9 shows a top view of the structure of FIG. 8.

With further reference to FIGS. 1, 2 and 14 along with FIGS. 3 and 8-12, a structure allowing posterior slope adjustment of the saw guide is generally designated by the reference numeral 80. As seen in FIGS. 1 and 2, a leg 81 extends generally outwardly from the forked legs 71, 73 of the structure 70 in a direction away from the intramedullary rod 11. The leg 81 includes a dovetail groove 82 designed to receive a slide mechanism 85 seen in FIGS. 8 and 9 as well as in FIG. 3. As shown in FIG. 8, the slide mechanism 85 includes an elongated slot 87 in which rides a pin 84 (FIGS. 1 and 2) which pin also rides in a slot 86 extending perpendicularly to the longitudinal extent of the leg 83 which extends parallel to the longitudinal extent of the leg 81. Thus, sliding movements of the slide 85 cause the pin 84 to be reciprocated up and down with respect to the longitudinal extent of the slot 86.

Figure 10:
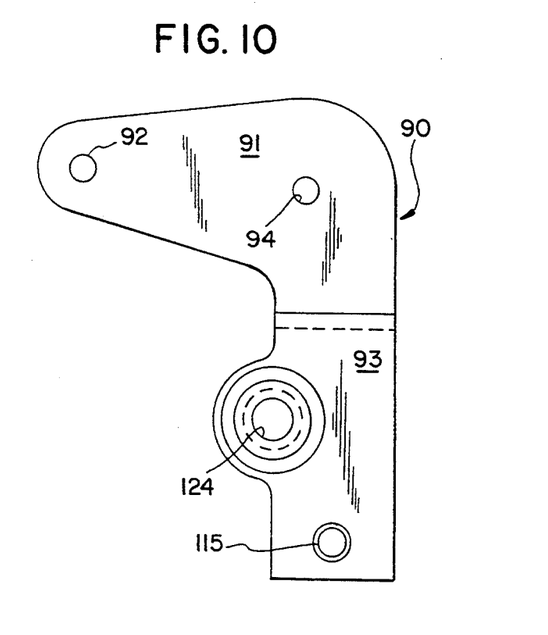
FIG. 10 shows a side view of an L-shaped arm which carries the saw guide while allowing posterior slope adjustment and quick release of the saw guide.
Figure 11:
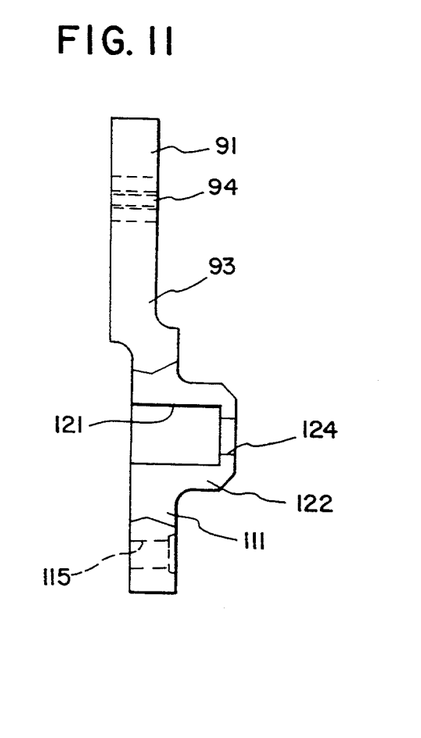
FIG. 11 shows a front view of the structure of FIG. 10.
Figure 12:
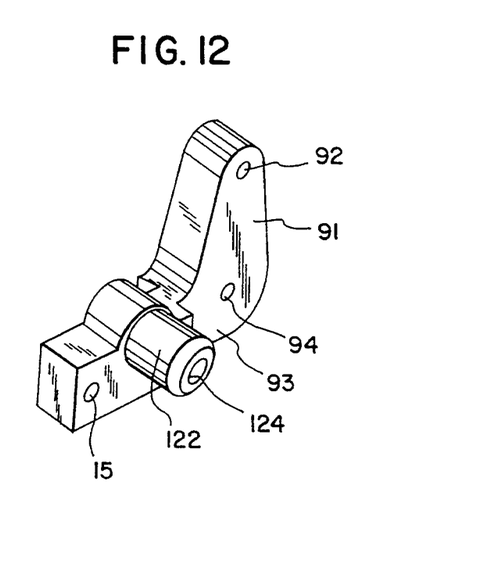
FIG. 12 shows a perspective view of the device illustrated in FIGS. 10 and 11.

With reference to FIGS. 10-12, an L-shaped support 90 is seen to include a short leg 91 and a long leg 93. The short leg 91 has a terminus where a hole 92 is located. With reference back to FIG. 2, it is seen that the pin 84 not only extends through the grooves 86 and 87 but also extends through the hole 92 in the short leg 91 of the L-shaped support 90. Additionally, at the intersection of the legs 91 and 93 of the support 90, a further hole 94 is provided through which extends a pin 88, which pin 88 also engages openings in the legs 81, 83 including the opening 97 in the leg 83 as seen in FIGS. 1 and 2. Thus, movements of the slide 85 within the dovetail groove 82 result in movements of the pin 84 within the groove 86 thereby causing pivoting movements of the support 90 with respect to the pivot pin 88. Thus, sliding movements of the slide 85 within the dovetail groove 87 will facilitate posterior slope adjustments of the saw guide 110.

With particular reference to FIG. 3, it is seen that the dovetail groove 82 receives a dovetail projection 101 of the slide 85. A blind bore 103 in the slide 85 receives a spring 102 which presses a ball 104 against the bottom of the dovetail groove 82. With reference to FIG. 14, it is seen that the bottom of the dovetail groove 82 has a plurality of part spherical depressions 95, 96, 98, 99 and 100 of which the depression 99 is seen in FIG. 3. Thus, as the slide 85 is slid along the dovetail groove 82, the ball 104 may enter any one of these recesses to firmly fix the position of the slide 85 and, correspondingly, the particular posterior slope adjustment of the saw guide 110. As seen in FIG. 1, indicia 106 are provided on the leg 81 so that the user will know which recess of the recesses 95, 96, 98, 99 and 100 is receiving the ball 104 and, thereby, which particular angle of posterior slope adjustment has been selected.

Figure 15:
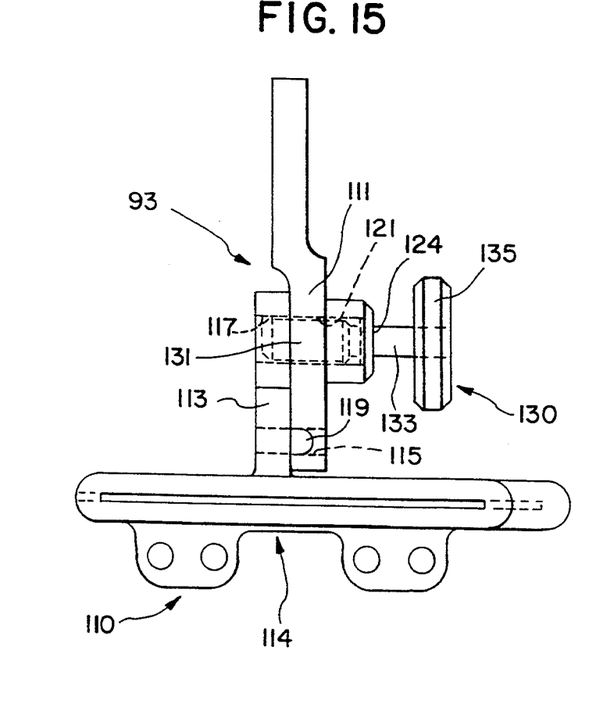
FIG. 15 shows a front view of the structure illustrated in FIGS. 10-12 including the saw guide detachably connected thereto.

With reference, now, to FIGS. 1, 4-7, 10-12 and 15, it is seen that the support 90 elongated leg 93 is formed of two parts including, with particular reference to FIG. 15, the proximal portion 111 and the distal portion 113, with these portions being releasably connectable together. For this purpose, the distal portion 113 includes a passageway 115 having a smooth inner periphery as well as a passageway 117 having a threaded inner periphery. The proximal end 111 of the elongated leg portion 93 carries a pin 119 which is fixed to the leg portion 111 and which may enter the passageway 115 of the leg portion 113. As particularly shown in FIGS. 1 and 15, the leg portion 113 carries the saw guide 110. With the pin 119 entering the passageway 115, and with the passageway 117 aligned with a further threaded passageway 121 formed in the leg 111, a threaded rod 130 having an enlarged threaded portion 131 connected to an actuator knob 135 via a narrow neck portion 133 may be rotated to cause the threaded portion 131 to enter the passageway 117 to couple the legs 111 and 113 together. When it is desired to remove the saw guide 110 from the rest of the instrument, one need only rotate the knob 135 in the counterclockwise direction, thereby unthreading the threaded portion 131 out of the threaded passageway 117 so that with a simple rotative motion, the pin 119 may be removed from the passageway 115 to remove the rest of the instrument from the saw guide 110.

As best seen with reference to FIG. 11, the passageway 121 is formed partially within a protruding portion 122 of the leg 111 which protruding portion has a smaller diameter opening 124 therethrough allowing the neck 133 of the actuating knob 130 to slidably move therethrough.

With reference, now, to FIGS. 1, 4–7 and 15, further details of the saw guide 110 will be described. As best seen in FIGS. 4, 5 and 15, the saw guide 110 is of generally T-shaped configuration with the leg of the "T" comprising the leg 113. The crosspiece 141 has an arcuate tibia engaging surface 143 (FIGS. 1 and 6) with the opposite side thereof 145 being flat and having the opening of an elongated slot 147 designed to guide a surgical saw in cutting movements on the proximal tibia. The additional arcuately curved surface 144 is designed to engage the proximal tibia in any prescribed angle of posterior slope adjustment of the saw guide 110. As should be understood from FIG. 7, the surface 144 is curved in two degrees of freedom including (1) in the plane of the drawing sheet and (2) in a plane perpendicular thereto as evidenced by the phantom line 146 showing the upward extent of curvature in the view of FIG. 7. These curvatures provide optimal engagement of the saw guide 110 with the complex curved surface of the proximal tibia regardless of tibial size and posterior slope adjustment of the instrument. In operation, the surface 143 engages the proximal tibia with a surface contact while the surface 144 engages the proximal tibia with a linear contact. As seen in these figures, projecting portions 151 and 153 are provided with the projection 151 including pin receiving holes 155 and 157, with the projection 153 having pin receiving holes 159 and 161. As should be understood by those skilled in the art, the pin receiving holes 155, 157, 159 and 161 are sized to receive surgical pins which may be guided therethrough and into the proximal tibia to affix the saw guide 110 in a desired position and configuration. The cutting head 110 has an angulated cutting slot 147 with the flat anterior surface 145 being shorter than the multiple arcuate posterior surface 143. The angle alpha 149 between these two surfaces is important to allow angulation of the surgical saw to resect a larger sized proximal tibial surface. This angulation and the thinness of the cutting head allows insertion of the cutting head beneath the patellar fat pad facilitating application of the cutting head on the proximal tibia.

Figure 16:
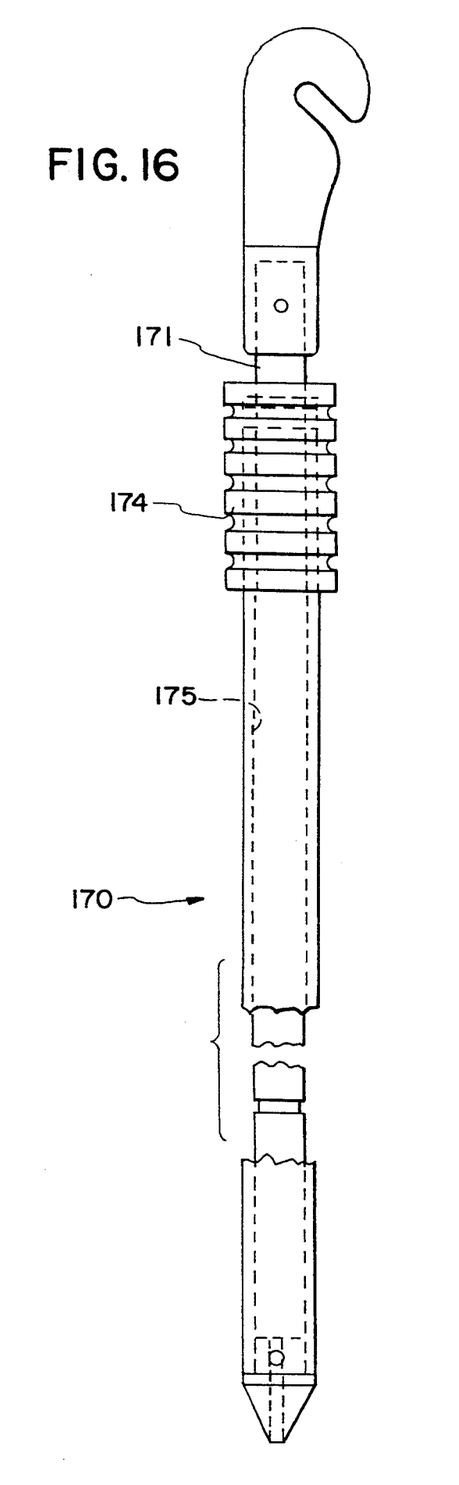
FIG. 16 shows a side view, partially in phantom, of the elongated telescoping medial-lateral adjustment rod.

With reference, now, to FIGS. 2 and 16, it is seen that an elongated telescoping rod 170 is provided to assist in facilitating accurate medial-lateral adjustment of the instrument. The rod 170 includes a proximal end 171 received within a recess 175 formed in a distal end 173. The proximal rod 171 includes a proximal end 177 formed in the shape of a hook having a hook recess 179 designed to be removably receivable on a pin 172 extending between the legs 81, 83 of the structure 80 as best with reference to FIG. 1.

As so attached, medial-lateral movements of the rod 170 will result in corresponding medial-lateral movements of the structure 70, 80 when the knob 79 is suitably loosened. The lower rod 173 has a gripping portion 174 which is suitably structured to facilitate firm grip. The distal end of the distal rod 173 has a generally pointed end 176 facilitating engagement with the ankle of the patient so that the mechanical axis of the patient's tibia may be accurately determined. With the knob 79 suitably loosened, the rod 170 may be telescoped until the distal end 176 engages the center of the patient's ankle whereupon medial-lateral movements of the rod 170 may be carried out until alignment in the medial-lateral direction with the mechanical axis of the tibia is achieved, whereupon the knob 79 may be suitably tightened to fix the position and orientation of the instrument 10 in the medial-lateral direction. After the knob 79 has been tightened with the proper medial-lateral position and orientation of the instrument 10 having been achieved, the telescoping rod 170 may easily be removed merely by lifting the slot 179 off the pin 172.

With the present invention having been described in terms of its structure, in great detail, the particular aspects of the operation of the instrument will now be described in a comprehensive manner.

In applying the inventive instrument to the proximal tibia, a hole is drilled centrally of the proximal tibia at the anterior edge of the anterior tibial spine. With the entire instrument assembled together, the intramedullary rod 11 is inserted through the hole until the rod 11 bottoms out on bone at the anterior tibial spine. For this purpose, a shoulder 6 is provided at the distal end of the proximal end 13 of the rod 11. As the rod 11 is being inserted, the recesses 17 promote evacuation of compressed intramedullary fat, thereby minimizing the threat of a fat embolism.

With the rod 11 properly inserted with the shoulder 6 engaging the top of the proximal tibia, the sleeve 30 may be moved along the bar 20 to adjust the position of the saw guide 110 in the anterior-posterior direction on the anterior surface of the tibia. The frictional interengagement of the slots 32 with the outer surface of the bar 20 will retain the sleeve 30 in a desired position along the bar 20.

With the anterior-posterior adjustment having been made, the slide mechanism 85 is moved along the dovetail groove 82 to adjust the posterior slope of the saw guide 110 through pivoting of the L-shaped support 90 about the pivot pin 88. For this purpose, the indicia 106, best seen in FIG. 1, will give the surgeon an indication of which one of the concave recesses 95, 96, 98, 99 or 100 (FIG. 14) is engaged by the ball detent 104 (FIG. 3).

With the posterior slope of the saw guide 110 guide slot 147 having been set, the vertical position of the saw guide 110 may be adjusted by rotation of the knob 60 with the resultant vertical reciprocation of the rod 50 and all structure carried thereby. The pitch of the interacting threads between the knob 60 and the rod 50 is set so that the knob 60 acts as a micrometer-type knob, requiring a number of rotations for a small distance of reciprocation, thereby permitting extremely fine adjustment of the height of the saw guide 110 and, thereby, the depth of the cut on the proximal tibia.

With the height of the saw guide 110 having been set, the knob 79 may be loosened so that medial-lateral adjustment of the saw guide 110 may be carried out. With the knob 79 loosened, the telescoping rod 170 is attached over the pin 172 using the slot 179 and the distal portion of the rod 173 is extended until the distal tip 176 thereof may engage the center of the patient's ankle so that the position of the proposed cut may be aligned with respect to the mechanical axis of the patient's tibia. When the appropriate adjustment has been made, the knob 79 may be suitably tightened and the telescoping rod 170 may be removed and placed aside.

With all of these adjustments having been made, the saw guide 110 should be in the appropriate position to guide a surgical saw in the resection of the proximal tibia. In such position, pins (not shown) are inserted through the pin receiving holes 155, 157, 159 and 161 to firmly fixate the saw guide 110 on the proximal tibia.

Once the pins have been securely fastened, with reference to FIGS. 1 and 15, the knob 135 may be rotated until the threaded rod 131 leaves the opening 117 in the leg 113 whereupon the rest of the instrument may be easily removed from the saw guide 110 by rotating the pin 119 out of the hole 115 and with the intramedullary rod 11 being removed from the proximal tibia. At this point, the only portion of the instrument which remains on the patient is the T-shaped saw guide 110.

With the saw guide 110 remaining on the proximal tibia, the surgeon may utilize a reciprocating or saggital saw, as desired, to resect the proximal tibia.

If additional cuts are necessary, with the saw guide 110 retained in position on the proximal tibia, the rest of the instrument may be reattached with the rod 11 reinserted into the intramedullary canal of the proximal tibia and then the pins may be removed and further adjustment of the position and orientation of the saw guide 110 may be carried out with subsequent pinning and subsequent removal of the rest of the instrument from the saw guide 110.

The versatility of the present invention allows the surgeon to accommodate for variations in anatomy and for the patient's particular clinical problem. Thus, for example, lax ligaments with a severe valgus deformity frequently dictates a more stable knee design. Patients having osteoarthritis sometimes do not have a patella and require a versatile instrument in performing surgery. The ability to vary the posterior slope between 0° and 10° as well as to accommodate to all anterior-posterior, vertical, medial-lateral adjustments renders the present invention able to accommodate to any surgical situation. The particular shape of the saw guide 110 is specifically designed to better facilitate placement. When a patient has tight knees, it is sometimes difficult to locate the resection slot 147 beneath the patellar fat pad and near the center of the knee. Thus, the inventive saw guide 110 has been made with an extremely thin head which is angled, as shown in FIGS. 4–7, 25° to allow protection of the patellar fat pad and the anterior tendon and to offer a wider angle of resection posteriorly so that larger tibias may be suitably resected. The face of the slot abutting bone has a new radius allowing the close fit of the cutting slot to the bone regardless of the angle of resection. In the preferred embodiment, the slot has a height of 0.040 inches and is specifically designed to fit gall resistant blades having guide ribs with a spacing 0.038 inches, which blades are particularly described in U.S. Pat. No. 5,002,555. These blades may also be coated with the highly effective BRAZOL coating. BRAZOL is a registered trademark of Alvarado Orthopedic Research of San Diego, Calif.

As such, an invention has been disclosed in terms of a surgical instrument and method of use, which fulfill each and every one of the objects of the present invention as set forth hereinabove and provide a new and useful intramedullary universal proximal tibial resector guide of great novelty and utility.

Of course, various changes, modifications and alterations in the teachings of the present invention may be contemplated by those skilled in the art without departing from the intended spirit and scope thereof. As such, it is intended that the present invention only be limited by the terms of the appended claims.

I claim:
1. A proximal tibial resector guide, comprising:
    a) an intramedullary rod with a longitudinal axis and having a distal end adapted to be inserted within an intramedullary canal of a tibia, and a proximal end;
    b) a bar fixedly attached to said proximal end of said intramedullary rod and extending away therefrom in a direction perpendicular to said axis;
    c) a support structure slidably mounted on said bar for movements toward and away from said rod to provide adjustability of said guide in an anterior-posterior direction, said support structure carrying a saw guide having a saw guide slot and said support structure further including:
        i) posterior slope adjustment means for adjusting the posterior slope of said saw guide slot;
        ii) medial-lateral adjustment means for adjusting the orientation of said saw guide slot in the medial-lateral direction;
        iii) vertical adjustment means for infinitely adjusting vertical position of said saw guide with respect to said bar, said vertical adjustment means including an elongated vertically disposed sleeve having diametrically opposed slots receiving said bar, said sleeve having an internal passage slidably receiving an elongated threaded support rod, said elongated sleeve having a recess slidably receiving an actuator sleeve having an internal threaded passage threadably receiving said support rod, whereby rotations of said actuator sleeve result in reciprocation of said support rod and infinite adjustment of said vertical position of said saw guide; and
        iv) coupling means for detachably coupling said saw guide to said posterior slope adjustment means.

2. The invention of claim 1, wherein said intramedullary rod includes a shoulder adapted to rest on a proximal surface of said tibia, when said distal end of said rod is inserted into said intramedullary canal.

3. The invention of claim 3, wherein said support rod has an elongated slot aligned with said slots in said elongated sleeve and slidably receiving said bar, whereby said support rod is constrained against rotation.

4. The invention of claim 3, wherein said support rod is threaded at a proximal end thereof, said support rod having a distal end with a flat plate lying in a plane perpendicular to a direction of extension of said bar, said medial-lateral adjustment means including a coupling pivotably coupled to said flat plate.

5. The invention of claim 4, wherein said medial-lateral adjustment means further includes a rotary locking knob which may be loosened to permit pivoting of said coupling and which may be tightened to lock said coupling in a particular desired medial-lateral position of said saw guide.

6. The invention of claim 1, wherein said posterior slope adjustment means includes an L-shaped support including a first leg intersecting with a second generally downwardly depending leg at a pivot point, said first leg being coupled to an actuator for posterior slope adjustment, said second leg carrying said coupling means for detachably coupling said saw guide to said posterior slope adjustment means.

7. The invention of claim 6, wherein said saw guide coupling means includes a threaded rod threadably receivable through respective alignable holes on said saw guide and said second leg.

8. The invention of claim 7, wherein said saw guide includes a T-shaped body including a leg detachably attachable to said second leg and a crosspiece carrying said saw guide slot.

9. The invention of claim 1, wherein said saw guide includes a T-shaped body including a leg attachable to said posterior slope adjustment means and a crosspiece carrying said saw guide slot.

10. The invention of claim 9, wherein said crosspiece has a plurality of protrusions, each protrusion including a pin receiving passage.

11. The invention of claim 10, wherein said crosspiece has an arcuate proximal tibia engaging surface.

12. The invention of claim 1, wherein said medial-lateral adjustment means further includes an elongated rod detachably attachable to said support structure and alignable with an ankle of a patient's leg.

13. The invention of claim 12, wherein said elongated rod is comprised of two telescoping sections.

* * * * *

UNITED STATES PATENT AND TRADEMARK OFFICE
Certificate

Patent No. 5,342,368                                                        Patented: August 30, 1994

On petition requesting issuance of a certificate for correction of inventorship pursuant to 35 U. S. C. 256, it has been found that the above-identified patent, through error and without deceptive intent, improperly sets forth the inventorship.

Accordingly, it is hereby certified that the correct inventorship of this patent is: Thomas D. Petersen, La Mesa, Calif.; Richard A. Lane, Fort Wayne, Ind.; John R. Howard, Addison, Ill.; Chuck Nichols, Addison, Ill.; Todd S. Johnson, Fort Wayne, Ind.

Signed and Sealed this Seventh Day of October, 1997.

ROBERT A. HAFER
*Supervisory Patent Examiner*
Art Unit 1802